(12) United States Patent
Oh

(10) Patent No.: US 10,641,640 B2
(45) Date of Patent: May 5, 2020

(54) FUEL SENSOR FOR FLEXIBLE FUEL VEHICLE

(71) Applicant: Hyundai Motor Company, Seoul (KR)

(72) Inventor: Sun-Mi Oh, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 224 days.

(21) Appl. No.: 15/266,233

(22) Filed: Sep. 15, 2016

(65) Prior Publication Data

US 2017/0350747 A1 Dec. 7, 2017

(30) Foreign Application Priority Data

Jun. 7, 2016 (KR) .......................... 10-2016-0070139

(51) Int. Cl.
*G01F 23/22* (2006.01)
*G01F 23/296* (2006.01)
*G01N 33/22* (2006.01)
*G01N 29/024* (2006.01)

(52) U.S. Cl.
CPC ....... *G01F 23/2968* (2013.01); *G01N 29/024* (2013.01); *G01N 33/22* (2013.01); *G01F 23/2962* (2013.01); *G01N 2291/022* (2013.01); *G01N 2291/02836* (2013.01)

(58) Field of Classification Search
CPC ...... G01F 22/00; G01F 23/268; G01F 23/296; G01F 23/2962; G01F 23/2968; G01F 23/28; G01N 9/00; G01N 29/024; G01N 33/22; G01N 33/2829; G01N 2291/022; G01N 2291/02836; B60W 10/00; F02D 41/0025; Y10T 29/49826
See application file for complete search history.

(56) References Cited

U.S. PATENT DOCUMENTS

| | | | | |
|---|---|---|---|---|
| 5,315,563 A | * | 5/1994 | Lichtenfels, II | ........ G01F 23/00 367/165 |
| 8,072,229 B2 | * | 12/2011 | Nakamura | ............ F02D 33/003 324/663 |
| 2014/0318646 A1 | * | 10/2014 | Song | .................... F02D 41/3082 137/560 |

FOREIGN PATENT DOCUMENTS

| | | | |
|---|---|---|---|
| GB | 2410799 A * | 8/2005 | ......... G01F 23/2962 |
| JP | H09-109700 A | 4/1997 | |
| KR | 10-0987337 B1 | 10/2010 | |
| KR | 10-1205234 B1 | 11/2012 | |
| KR | 10-1481264 B1 | 1/2015 | |
| KR | 10-1559123 B1 | 10/2015 | |
| KR | 10-2016-0013683 A | 2/2016 | |
| KR | 10-1599666 B1 | 3/2016 | |
| KR | 10-1620845 B1 | 5/2016 | |

OTHER PUBLICATIONS

English translation of KR 101620845 B1.*

(Continued)

*Primary Examiner* — Eric S. McCall
(74) *Attorney, Agent, or Firm* — Mintz Levin Cohn Ferris Glovsky and Popeo, P.C.; Peter F. Corless

(57) ABSTRACT

A sensor detects a fuel level and fuel concentration in a fuel tank of a flexible fuel vehicle (FFV) that uses flexible fuel such as ethanol fuel or alcohol fuel. The fuel sensor includes: a level sensor which is inserted into a lower surface of a pump module housing; and a concentration sensor which is mounted on a side surface of the pump module housing.

3 Claims, 6 Drawing Sheets

(56) References Cited

OTHER PUBLICATIONS

English translation of KR 101599666 B1.*
English translation of KR 20160013683 A.*
Non-Patent Literature "Transducer Beam Spread", archived on Sep. 4, 2014, accessible at http://web.archive.org/web/20140904034033/https://www.nde-ed.org/EducationResources/CommunityCollege/Ultrasonics/EquipmentTrans/beamspread.htm.*

* cited by examiner (a)          (b)

(a)          (b)

(a)

(b)

(c)

(d)

(e)

(f)

(a)  (b)

(a)  (b)

FUEL SENSOR FOR FLEXIBLE FUEL VEHICLE

CROSS-REFERENCE TO RELATED APPLICATION

This application claims under 35 U.S.C. § 119(a) the benefit of Korean Patent Application No. 10-2016-0070139, filed on Jun. 7, 2016 in the Korean Intellectual Property Office, the entire contents of which are incorporated by reference herein.

BACKGROUND

1. Technical Field

The present invention relates to a sensor for detecting a fuel level and a fuel concentration in a fuel tank of a flexible fuel vehicle (FFV) that uses flexible fuel such as ethanol fuel or alcohol fuel.

2. Description of the Related Art

Recently, to reduce the dependence on petroleum in order to address problems of exhaustion of fossil fuels, there has been an increased focus on alternative fuels. In particular, the number of vehicles driven by fuel made by mixing ethanol or alcohol fuel with gasoline has rapidly increased, thus promoting environmentally-friendly driving of the vehicles by reducing emissions of carbon in vehicle exhaust gas.

An environmentally-friendly vehicle capable of utilizing ethanol or alcohol fuel is called a flexible fuel vehicle (FFV), and an engine or the like of the existing gasoline vehicle needs to be modified because the FFV vehicle uses ethanol or alcohol fuel.

That is, in the case of the FFV vehicle, devices in a fuel circulation system, such as a fuel tank, a fuel pump, injection nozzles, and valves, need to be changed to devices made of materials that endure alcohol well, and alcohol-resistant engine oil and alcohol-resistant filters need to be used.

A float type contact sensor, which detects the residual amount of fuel in the fuel tank of an existing gasoline vehicle, needs to be changed to a hermetic structure or a contactless sensor, because the existing float type contact sensor does not ensure durability of materials resistant to alcohol fuel, and a special alcohol sensor needs to be mounted to detect a concentration of alcohol in fuel so as to adjust the injection amount of fuel, ignition timing, and the like.

As one of the methods of measuring the amount of automobile fuel in the related art, there is a method that adopts a contact sensor using a float arm. The contact sensor utilizes a contact point on a sensor board that is moved in accordance with a height of the float arm in the fuel, and a fuel level is converted into a predetermined resistance value. There is a drawback in that this method is difficult to apply because of corrosion of the sensor board and the contact point which is caused when fuel containing alcohol is used.

As another method in the related art, there is a method that adopts a contactless fuel sensor using a Hall sensor. Similar to the contact sensor, this method also incorporates a sensor having a float arm, but prevents contact between the Hall sensor and fuel in order to prevent corrosion in the alcohol fuel, and solves a problem of malfunction caused by abrasion of the contact point and electrodes. However, there is a drawback in that the aforementioned method using the Hall sensor results in an increase in manufacturing costs in comparison with a method using the existing sensor.

An alcohol concentration detecting sensor, which is currently applied to the FFV vehicle, adopts a principle that a change in permittivity between two electrodes is detected in accordance with an alcohol concentration.

U.S. Pat. No. 6,993,967 relates to a liquid level sensor applied to an automobile fuel tank, in which an ultrasonic transceiver for measuring a level of a liquid is provided, and a reference unit transmits a reference signal and determines a level by comparing signals in two channels. According to this method, there are drawbacks in that two electrodes need to be formed on an ultrasonic element, and a signal of a liquid level may be inaccurately measured when the fluid greatly sloshes and slopes.

Korean Patent Application Laid-Open No. 10-2007-7023851 relates an apparatus for measuring a liquid level in a container by using an ultrasonic transducer, in which the transducer is positioned to be spaced apart from a bottom, the transducer irradiates toward a liquid surface, the transducer is integrated with a housing, and an integrated switching circuit ASIC is positioned in the housing. The level sensor has a drawback in that a signal of a liquid level may be inaccurately measured when the fluid greatly sloshes and slopes as described above.

Korean Patent Application Laid-Open No. 10-2013-0060565 discloses a method that determines whether to refuel a vehicle by analyzing an oxygen concentration detected by an oxygen sensor, performs ethanol concentration learning if it is determined that the vehicle is newly refueled, corrects the amount of fuel based on the learned ethanol concentration, and performs a feedback control associated with an air-fuel ratio in order to detect an ethanol concentration in the FFV vehicle. However, the aforementioned method has a drawback in that if the ethanol concentration is not accurately calculated, engine start performance and driving performance of the 1-1-V vehicle deteriorate.

Therefore, there is a need for a multifunctional sensor that detects a fuel level and a fuel concentration in a fuel tank of an FFV vehicle in order to solve the aforementioned problems in the related art.

SUMMARY

The present invention provides a multifunctional sensor for an FFV vehicle, which is capable of ensuring fuel resistance and corrosion resistance in comparison with the existing level sensor, and implementing optimal combustion in an engine by accurately measuring an ethanol content in flexible fuel.

An exemplary embodiment of the present invention provides a fuel sensor for a flexible fuel vehicle (FFV), the fuel sensor including: a level sensor which is inserted into a lower surface of a pump module housing; and a concentration sensor which is mounted on a side surface of the pump module housing.

In the present invention, the level sensor may be mounted vertically on a level sensor damper of the pump module housing.

In the present invention, the level sensor may have a level sensor stopper, and the level sensor stopper may be mounted to be coupled to a level sensor damper slot formed in one surface of the level sensor damper.

In the present invention, a diameter of the level sensor damper may be equal to a diameter of a piezoelectric ceramic mounted on the level sensor.

In the present invention, the diameter of the piezoelectric ceramic mounted on the level sensor may be 10 to 15 mm.

In the present invention, the concentration sensor may be mounted horizontally on a concentration sensor damper of the pump module housing.

In the present invention, the concentration sensor may have a concentration sensor stopper, and the concentration sensor stopper may be mounted to be coupled to a concentration sensor damper slot formed in one surface of the concentration sensor damper.

In the present invention, a diameter of the concentration sensor damper may be greater than a diameter of a piezoelectric ceramic mounted on the concentration sensor.

In the present invention, the diameter of the piezoelectric ceramic mounted on the concentration sensor may be 6 to 10 mm.

In the present invention, a length of the level sensor damper may be 218 to 400 mm.

In the present invention, a length of the concentration sensor damper may be 40 to 80 mm.

In the present invention, the fuel sensor may further include: a plate which is mounted on an upper surface of the pump module housing; a printed circuit board (PCB) case which is mounted on an upper surface of the plate and includes a PCB therein; and a cover which covers an upper surface of the PCB case.

In the present invention, an O-ring may be provided between the plate and the PCB case.

Another exemplary embodiment of the present invention provides a method of manufacturing a fuel sensor for an FFV vehicle, the method including: forming terminals of a level sensor or a concentration sensor by insert injection molding; forming a housing of the level sensor or the concentration sensor by injection molding; inserting a piezoelectric ceramic resonator into a piezoelectric ceramic insertion portion formed in the housing of the level sensor or the concentration sensor; inserting epoxy resin into the piezoelectric ceramic insertion portion and curing the epoxy resin; and laser-welding a cover on the piezoelectric ceramic insertion portion with the cured epoxy resin.

In the present invention, the method may further include mounting the level sensor on a level sensor damper of a pump module housing or mounting the concentration sensor on a concentration sensor damper of the pump module housing.

According to the multifunctional sensor for an FFV vehicle according to the present invention, in comparison with the existing level sensor, it is possible to ensure that the multifunctional sensor has durability and corrosion resistance when the multifunctional sensor is immersed in the flexible fuel, and it is possible to implement optimal combustion in an engine by precisely measuring an ethanol content in the flexible fuel.

According to the present invention, the multifunctional sensor for an FFV vehicle has excellent level detection performance compared to the existing sensor, may detect the concentration in real time, may conveniently detect a fuel level and a fuel concentration because the level sensor and the concentration sensor are mounted directly on the pump module housing, and may reduce manufacturing costs.

DETAILED DESCRIPTION OF THE EMBODIMENTS

Figure 1:
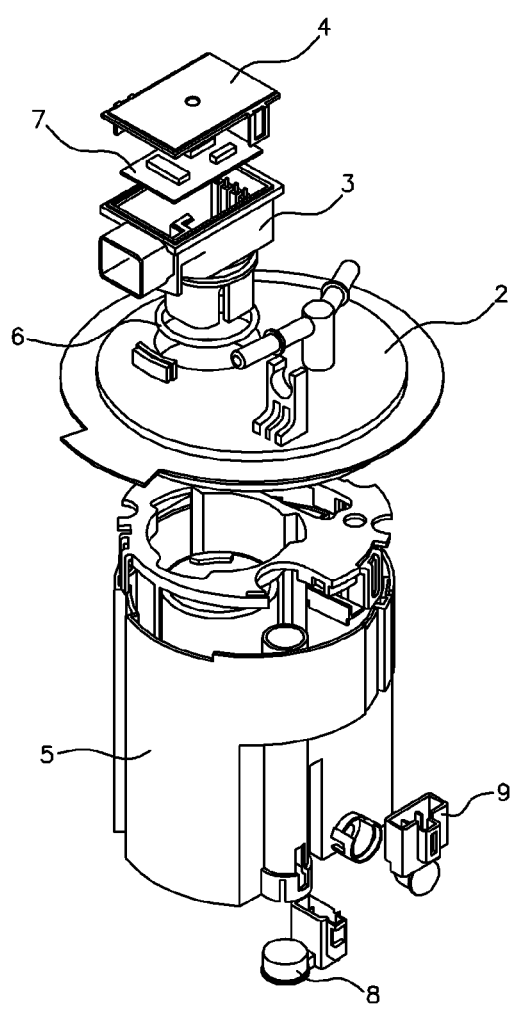
FIG. 1 is an exploded parts view of a fuel sensor for an FFV vehicle according to an exemplary embodiment of the present invention.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present invention may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Hereinafter, an exemplary embodiment of the present invention will be described in detail with reference to the accompanying drawings. Terms or words used in the specification and the claims should not be interpreted as a general and dictionary meaning and should be interpreted as a meaning and a concept which conform to the technical spirit of the present invention based on a principle that an inventor can appropriately define a concept of a term in order to describe his/her own invention by the best method. Therefore, the exemplary embodiments disclosed in the present specification and the configurations illustrated in the drawings are just the best preferred exemplary embodiments of the present invention and do not represent all the technical spirit of the present invention. Accordingly, it should be appreciated that various equivalents and modified examples capable of substituting the exemplary embodiments may be made at the time of filing the present application.

To solve the aforementioned problems in the related art, the present invention can ensure fuel resistance and corrosion resistance in comparison with the related art, and implement optimal combustion in an engine by precisely measuring an ethanol content in flexible fuel.

FIG. 1 is an exploded parts view of a fuel sensor for an FFV vehicle according to an exemplary embodiment of the present invention.

A multifunctional fuel sensor for a flexible fuel vehicle (FFV) according to the present invention includes a level sensor 8 which is inserted into a lower surface of a pump module housing 5, and a concentration sensor 9 which is mounted on a side surface of the pump module housing 5.

The present invention may further include a plate 2 which is mounted on an upper surface of the pump module housing 5, a printed circuit board (PCB) case 3 which is mounted on an upper surface of the plate 2 and includes a PCB 7 therein, and a cover 4 which covers an upper surface of the PCB case 3. An O-ring 6 may be provided between the plate 2 and the PCB case 3 so as to mitigate impact caused when the vehicle is driven.

As described above, the present invention has a structure in which the sensors for detecting a fuel level and a fuel concentration are integrally mounted in the pump module housing 5 which is referred to as 'R-CUP', thereby simultaneously measuring a fuel level and a concentration of ethanol or alcohol in fuel only by using the single housing.

The level sensor 8 and the concentration sensor 9 are manufactured integrally with the pump module housing 5 instead of being separately mounted in a fuel tank, and dampers are formed on the side surface and the lower surface of the pump module housing 5, and as a result, the level sensor 8 and the concentration sensor 9 may be conveniently attached and detached. That is, even if the level sensor 8 or the concentration sensor 9 malfunctions, each sensor may be simply replaced, and thus the fuel sensor may be easily repaired and used over a long period of time.

Meanwhile, the PCB 7, which processes sensor signals from the level sensor 8 and the concentration sensor 9 according to the present invention, is positioned on the plate 2 attached onto the upper surface of the pump module housing 5, unlike the level sensor 8 and the concentration sensor 9 which are immerged in the ethanol fuel, and as a result, the PCB 7 is durable and resistant to the ethanol fuel.

As described below, the fuel sensor has been made such that sensor elements (piezoelectric ceramic) of the level sensor 8 and the concentration sensor 9 are protected by a cover portion formed by laser welding, and as a result, sensor performance may be maintained even though the sensor elements are immerged in the ethanol fuel over a long period of time.

Figure 2:
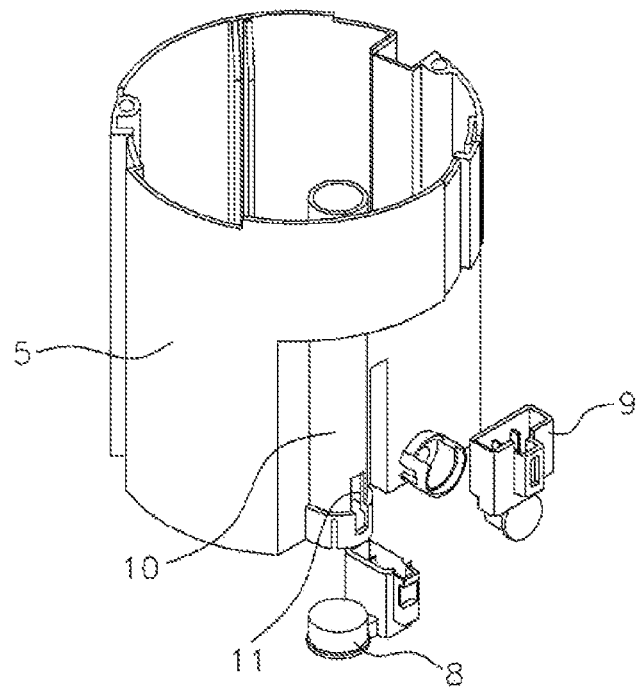
FIG. 2 is a perspective view illustrating a pump module housing, a level sensor, and a concentration sensor according to the exemplary embodiment of the present invention.

FIG. 2 is a perspective view illustrating the pump module housing, the level sensor, and the concentration sensor according to the exemplary embodiment of the present invention.

At least one level sensor damper 10 is provided on the side surface of the pump module housing 5 according to the present invention, and at least one concentration sensor damper 12 is provided on the lower surface of the pump module housing 5.

Figure 3:
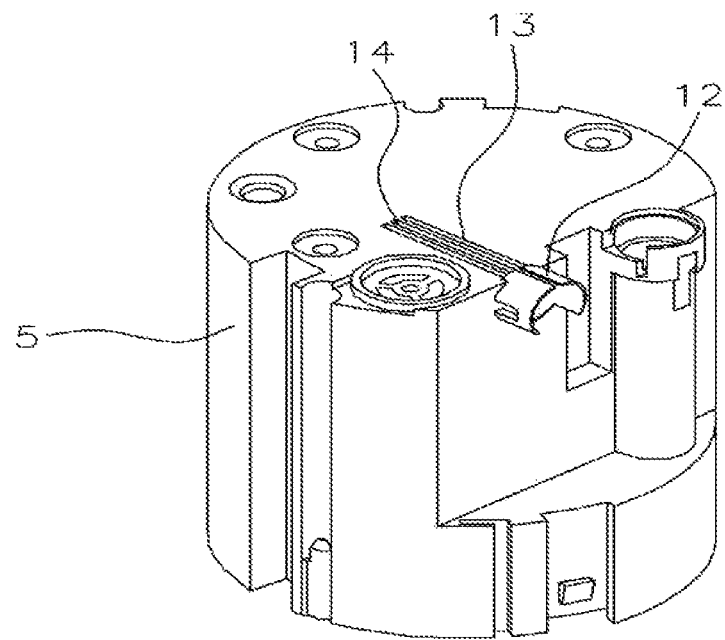
FIG. 3 is a perspective view illustrating a lower surface of the pump module housing according to the exemplary embodiment of the present invention.

The level sensor damper 10 and the concentration sensor damper 12 serve to couple and guide the level sensor 8 and the concentration sensor 9, respectively, and may also serve as passageways along which the fuel flows in and out. Meanwhile, as shown in FIGS. 2-3, fuel entrance holes 11 and 13 are formed in side surfaces of the level sensor damper 10 and the concentration sensor damper 12 according to the present invention, thereby allowing the fuel to easily flow in and out when the vehicle is refueled.

The level sensor damper 10 may be formed in a cylindrical shape, and the fuel entrance hole 11 is formed in one surface of the level sensor damper 10, thereby allowing a fuel level to be easily detected.

As can be seen in FIG. 2, the level sensor 8 is configured to be mounted vertically on the level sensor damper 10 of the pump module housing 5, and the level sensor 8 may be detachably coupled to the level sensor damper 10.

Meanwhile, a diameter of the level sensor damper 10 may be equal to a diameter of the piezoelectric ceramic mounted on the level sensor 8.

The reason is that if a diameter of the piezoelectric ceramic is excessively large, a width of the ultrasonic beam is decreased, such that straightness of an ultrasonic beam is optimized, and if a diameter of the piezoelectric ceramic is excessively small, a width of the ultrasonic beam is increased, such that a large number of ultrasonic beams are reflected by the damper and thus lost.

That is, in the present invention, since the diameter of the level sensor damper 10 is equal to the diameter of the piezoelectric ceramic, it is possible to minimize a loss of ultrasonic beams, and to improve level measurement accuracy at an inclination angle such as sloshing under a vehicle driving condition.

Therefore, in the present invention, the level sensor damper 10 may have a length of 218 to 400 mm, and as a result, a diameter of the piezoelectric ceramic may be about 10 to 15 mm considering the length of the level sensor damper 10 in order to detect a fuel level.

As a result, the level sensor 8 and the concentration sensor 9 according to the present invention are mounted in a fuel line between the fuel tank and an injector, and detect an alcohol concentration or an ethanol concentration in FFV fuel. Since the level sensor damper 10 and the concentration sensor damper 12 serve to guide the respective sensors, a fuel level may be accurately detected even though the fuel sloshes when the vehicle travels on a slope or the like.

FIG. 3 is a perspective view illustrating the lower surface of the pump module housing according to the exemplary embodiment of the present invention.

As described above, at least one concentration sensor damper 12 is provided on the lower surface of the pump module housing 5 according to the present invention, and the concentration sensor damper 12 serves to couple and guide the concentration sensor 9, and also serves as an entrance passageway for fuel.

The concentration sensor damper 12 may be formed in a cylindrical shape having a circular cross section, and the fuel entrance hole 13 is formed in one surface of the concentration sensor damper 12, thereby allowing a fuel concentration to be easily detected.

As can be seen in FIGS. 2-3, the concentration sensor 9 is configured to be mounted horizontally on the concentration sensor damper 12 of the pump module housing 5, and the concentration sensor 9 may be detachably coupled to the concentration sensor damper 12.

Because the concentration sensor 9 is always immersed in the fuel, the concentration sensor 9 is mounted horizontally with the fuel tank in order to detect a change in sound velocity for detecting a concentration.

As described above, the concentration sensor damper 12 is horizontally installed at a lower end of the pump module housing 5, and may assist the concentration sensor 9 in sufficiently measuring a concentration even when the residual amount of fuel is relatively small.

Meanwhile, in order to make it easy to newly detect a concentration and allow the fuel to easily flow in and out in a case in which the vehicle is newly refueled, the fuel entrance hole 13 may be formed to be horizontal with a lower end surface of the concentration sensor damper 12.

The concentration sensor damper 12 has a predetermined detection distance, and a length thereof may be 40 to 80 mm. In addition, a reflective plate insertion portion 14 is formed in the concentration sensor damper 12, and a reflective plate is inserted into the reflective plate insertion portion 14 so as to improve transmitting and receiving sensitivity for ultrasonic beams.

To allow the fuel to easily flow in and out in order to newly detect a concentration in a case in which the vehicle is newly refueled, a horizontal straight hole is formed at a lower end of the concentration sensor damper.

Meanwhile, in the present invention, a diameter of the concentration sensor damper 12 is greater than a diameter of the piezoelectric ceramic mounted on the concentration sensor 9, and since a fuel level is typically 15 mm when the residual amount of fuel is smallest, a size of the piezoelectric ceramic for the concentration sensor may be set to 6 to 10 mm smaller than the fuel level so that the piezoelectric ceramic may be always immerged in the fuel.

For reference, at the time of detecting an ethanol concentration, a difference in sound velocity property according to an ethanol concentration is decreased in a low-temperature region and increased in a high-temperature region, such that accuracy is improved when a temperature of fuel is 40° C. Therefore, in the present invention, to maintain a fuel temperature to 40° C. or higher, the concentration sensor 9 is mounted at the lower end of the pump module housing, such that the fuel with a temperature raised by an operation of a pump when the vehicle travels is used.

Figure 4:
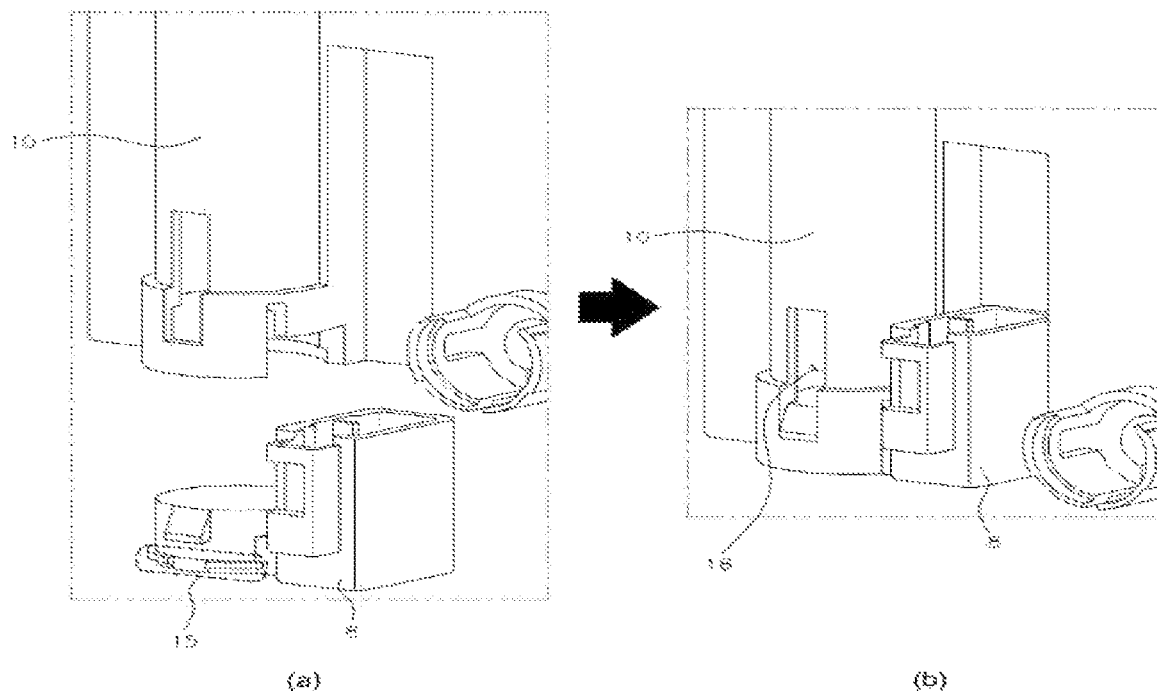
FIG. 4 is a perspective view illustrating a state in which the level sensor is being mounted on a level sensor damper according to the exemplary embodiment of the present invention.
Figure 5:
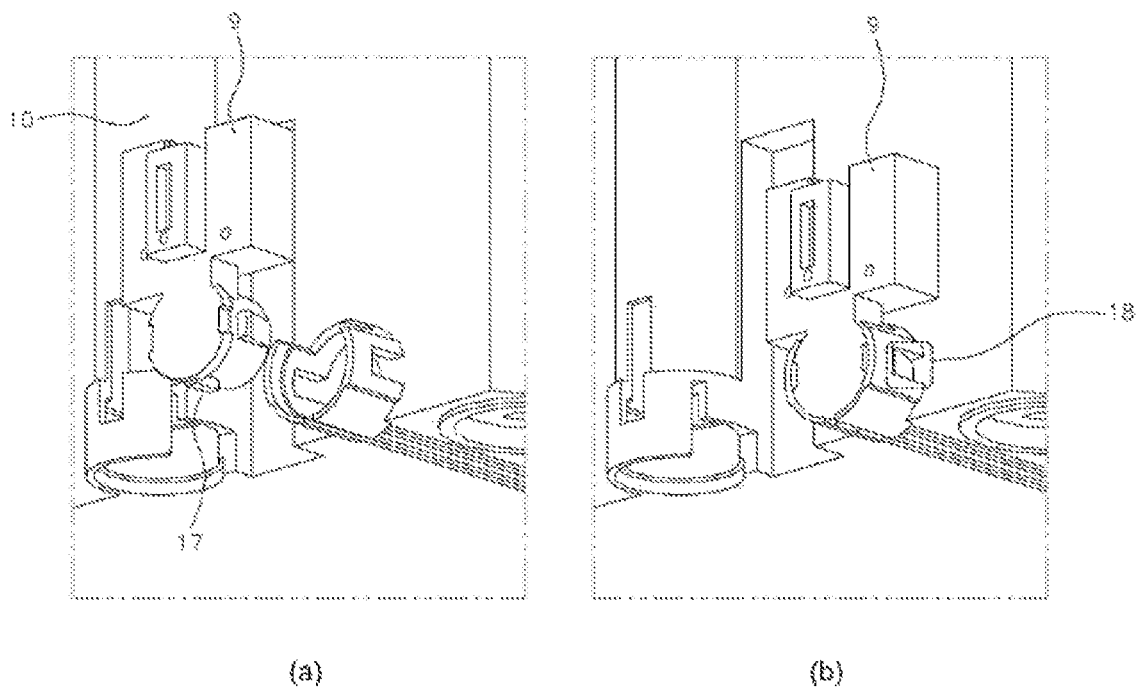
FIG. 5 is a perspective view illustrating a state in which the concentration sensor is being mounted on a concentration sensor damper according to the exemplary embodiment of the present invention.

FIG. 4 is a perspective view illustrating a state in which the level sensor is being mounted on the level sensor damper according to the exemplary embodiment of the present invention, and FIG. 5 is a perspective view illustrating a state in which the concentration sensor is being mounted on the concentration sensor damper according to the exemplary embodiment of the present invention.

As shown in FIG. 4, the level sensor 8 has at least one level sensor stopper 15, and the level sensor stopper 15 is mounted to be coupled to a level sensor damper slot 16 formed in one surface of the level sensor damper 10 That is, the level sensor 8 is inserted into the level sensor damper 10 and then rotated, such that the level sensor stopper 15 may be tightly coupled to the level sensor damper slot 16.

Likewise, as shown in FIG. 5, the concentration sensor 9 also has at least one concentration sensor stopper 17, and the concentration sensor stopper 17 is mounted to be coupled to a concentration sensor damper slot 18 formed in one surface of the concentration sensor damper 12. The concentration sensor 9 is inserted into the concentration sensor damper 12 and then rotated, such that the concentration sensor stopper 17 is tightly coupled to the concentration sensor damper slot 18.

As described above, the level sensor stopper 15 and the concentration sensor stopper 17 are provided to maintain a parallel state of the respective sensors. This structure is configured to improve transmitting and receiving sensitivity for ultrasonic beams and improve accuracy of level detection, and prevents deterioration in receiving sensitivity which may be caused when the ultrasonic beams are reflected from a liquid surface and then return to the ultrasonic sensor in a case in which the ultrasonic sensor is not mounted in parallel with the damper.

Figure 6:
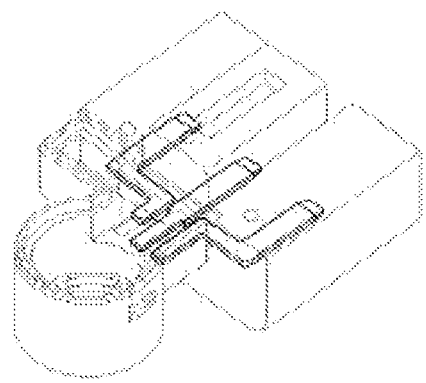
FIG. 6 is a perspective view sequentially illustrating states in which the concentration sensor according to the exemplary embodiment of the present invention is being manufactured.
Figure 6:
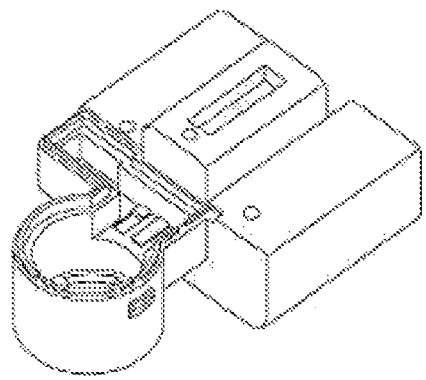
Figure 6:
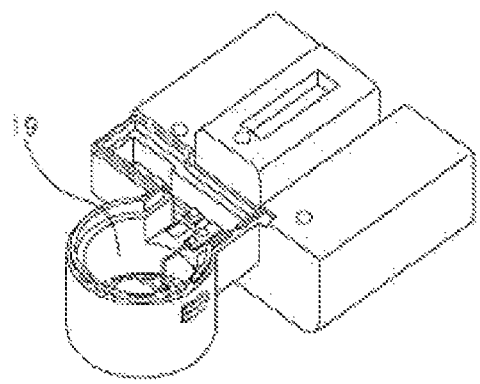
Figure 6:
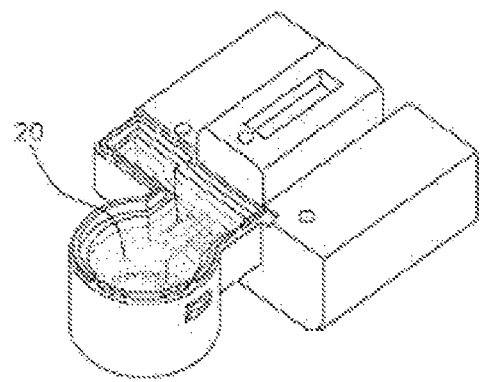
Figure 6:
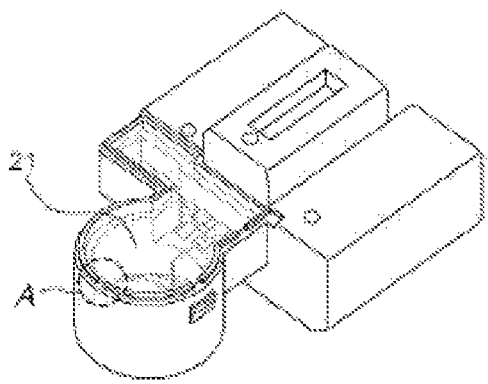
Figure 6:

FIG. 6 is a perspective view sequentially illustrating states in which the concentration sensor according to the exemplary embodiment of the present invention is being manufactured.

First, terminals of the level sensor or the concentration sensor are formed by insert injection molding (see FIG. 6 (a)), the housing of the level sensor or the concentration sensor is primarily formed by injection molding (see FIG. 6 (b)), and then a piezoelectric ceramic resonator is inserted into a piezoelectric ceramic insertion portion 19 formed in the housing of the level sensor or the concentration sensor (see FIG. 6 (c)).

Thereafter, epoxy resin 20 is inserted into and cured in the piezoelectric ceramic insertion portion 19 (see FIG. 6 (d)), and the cover is laser-welded on the piezoelectric ceramic insertion portion with the cured epoxy resin, and as a result, the level sensor or the concentration sensor is completely manufactured (see FIG. 6 (e)).

The level sensor manufactured as described above is mounted on the level sensor damper of the pump module housing or the concentration sensor manufactured as described above is mounted on the concentration sensor damper of the pump module housing, and as a result, the fuel sensor for an FFV vehicle according to the present invention is completely manufactured.

As described above, the present invention adopts the structure in which a level sensor or concentration sensor cover portion 21 is mounted at an upper end of the piezoelectric ceramic element and sealed by laser welding in order to prevent corrosion of the sensor housing and the piezoelectric ceramic element even though the fuel sensor is immerged in the ethanol fuel.

FIG. 6 (f) illustrates a cross section made by cutting part A of the level sensor or concentration sensor cover portion 21 illustrated in FIG. 6 (e), and a material is spread at the time of laser welding so as to form a structure having a trapezoidal cross section at a joint surface in order to increase joining force between the level sensor or concentration sensor cover portion 21 and the injection-molded product at the time of laser welding, and as a result, the joint surface becomes larger, and thus joining force is increased.

Figure 7:
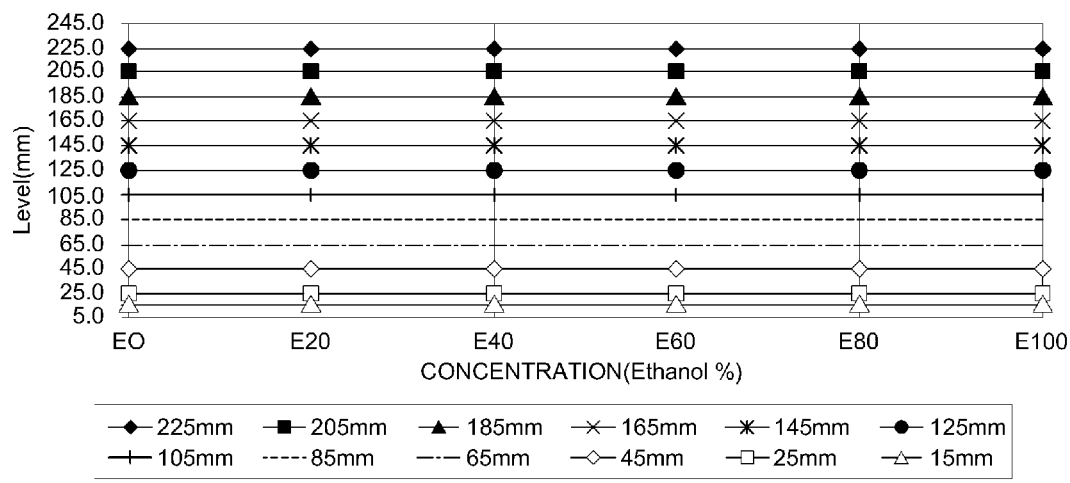
FIG. 7 is a graph illustrating a result of detecting a fuel level in accordance with a change in ethanol concentration by using the fuel sensor for an FFV vehicle according to the exemplary embodiment of the present invention.
Figure 8:
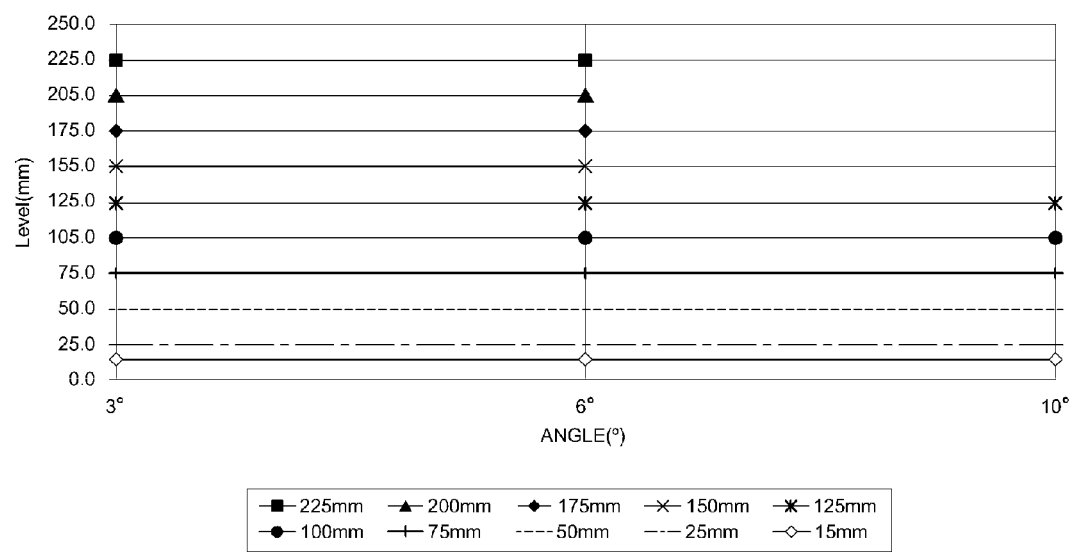
FIG. 8 is a graph illustrating a result of detecting a fuel level in accordance with a driving angle of the vehicle by using the fuel sensor for an FFV vehicle according to the exemplary embodiment of the present invention.

FIG. 7 is a graph illustrating a result of detecting a fuel level in accordance with a change in ethanol concentration by using the fuel sensor for an FFV vehicle according to the exemplary embodiment of the present invention, and FIG. 8 is a graph illustrating a result of detecting a fuel level in accordance with a driving angle of the vehicle by using the fuel sensor for an FFV vehicle according to the exemplary embodiment of the present invention.

As described above, in the present invention, since the diameter of the level sensor damper 10 is equal to the diameter of the piezoelectric ceramic, it is possible to minimize a loss of ultrasonic beams, and to improve level measurement accuracy at an inclination angle such as sloshing under a vehicle driving condition.

That is, since the level sensor damper 10 and the concentration sensor damper 13 serve to guide the respective sensors and increase coupling force with the respective sensors, a fuel level may be accurately detected even though the fuel sloshes when the vehicle travels on a slope or the like.

The level sensor 8 and the concentration sensor 9 according to the present invention are mounted in the fuel line between the fuel tank and the injector, and may more precisely detect an alcohol concentration or an ethanol concentration in FFV fuel.

Therefore, as shown in FIGS. 7 and 8, in the present invention, it can be confirmed that a fuel concentration and a fuel level may be precisely measured despite a change in fuel concentration or a change in angle of the vehicle.

Figure 9:
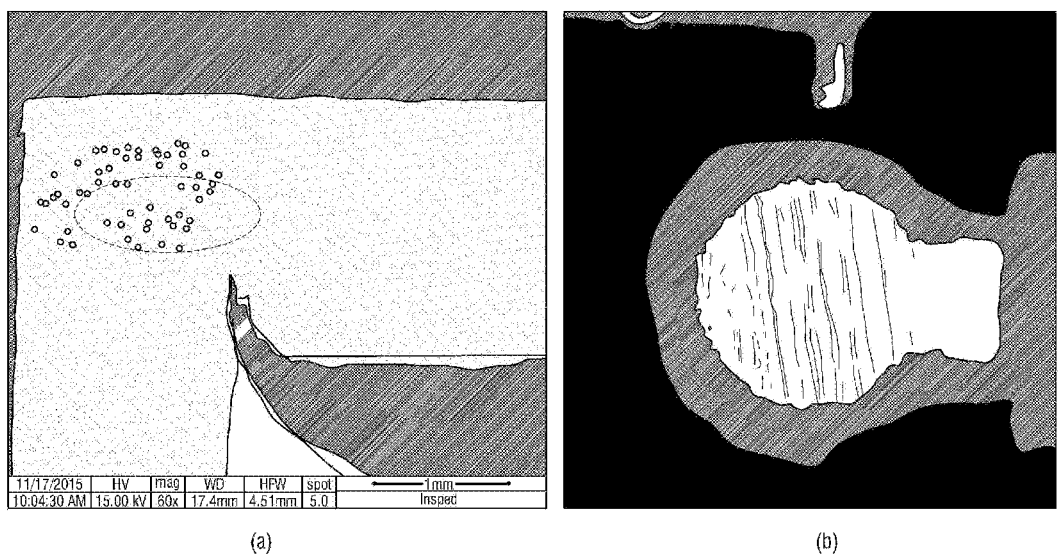
FIG. 9 is a photograph illustrating a state of an interface after the level sensor/concentration sensor according to the exemplary embodiment of the present invention is laser-welded.

FIG. 9 is a photograph illustrating a state of an interface after the level sensor/concentration sensor according to the exemplary embodiment of the present invention is laser-welded.

In particular, FIG. 9 (a) is a photograph illustrating the laser-welded cover portion of the sensor, and referring to a state of the interface after the laser welding, it can be seen that it is impossible to distinguish a joint interface to which a material is applied, and as a result, durability of the sensor is improved (see the part indicated by a dotted circle). In addition, referring to FIG. 9 (b), it can be seen that an image of the joint interface of the sensor is uniform.

Figure 10:
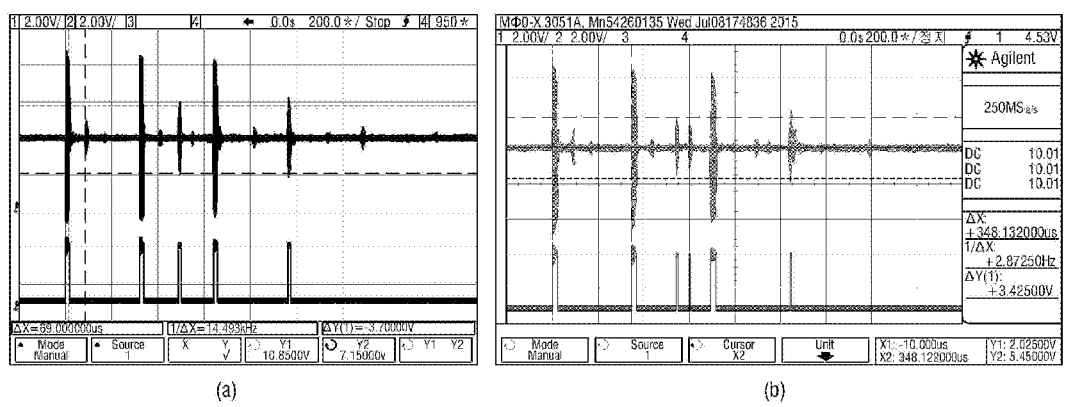
FIG. 10 is a graph illustrating changes in signals transmitted and received before and after the fuel sensor for an FFV vehicle according to the exemplary embodiment of the present invention is immerged in fuel.

FIG. 10 is a graph illustrating changes in signals transmitted and received before and after the fuel sensor for an FFV vehicle according to the exemplary embodiment of the present invention is immersed in fuel.

In particular, FIG. 10 (a) is a graph illustrating changes in ultrasonic signals transmitted and received before the sensor is immersed in the fuel, and FIG. 10 (b) is a graph illustrating changes in ultrasonic signals transmitted and received after the sensor is immersed in the fuel, and it can be seen that the signals transmitted and received before and after the sensor is immersed in the fuel are nearly coincident with each other. Therefore, according to the present invention, it can be seen that there is absolutely no problem with transmitting and receiving the ultrasonic signal.

According to the present invention, in comparison with the existing level sensor, it is possible to ensure that the fuel sensor has durability and corrosion resistance even when the fuel sensor is immersed in the flexible fuel, and it is possible to implement optimal combustion in an engine by precisely measuring an alcohol or ethanol content in the flexible fuel.

While the present invention has been described above with reference to the specific exemplary embodiment of the present invention, the exemplary embodiment is merely an example, and the present invention is not limited to the exemplary embodiment. The described exemplary embodiment may be changed or modified by those skilled in the art to which the present invention pertains without departing from the scope of the present invention, and may be variously modified and changed within the technical spirit of the present invention and within the scope equivalent to the appended claims.

What is claimed is:

1. A fuel sensor for a flexible fuel vehicle (FFV), the fuel sensor comprising:
   a level sensor which is inserted into a lower surface of a pump module housing; and
   a concentration sensor which is mounted on a side surface of the pump module housing,
   wherein the level sensor is mounted vertically on a level sensor guide of the pump module housing,
   wherein the level sensor has a level sensor stopper, and the level sensor stopper is mounted to be coupled to a level sensor guide slot formed in one surface of the level sensor guide,
   wherein the diameter of a first piezoelectric ceramic mounted on the level sensor is 10 to 15 mm,
   wherein the concentration sensor is mounted horizontally on a concentration sensor guide of the pump module housing,
   wherein the concentration sensor has a concentration sensor stopper, and the concentration sensor stopper is mounted to be coupled to a concentration sensor guide slot formed in one surface of the concentration sensor guide,
   wherein the diameter of a second piezoelectric ceramic mounted on the concentration sensor is 6 to 10 mm,
   wherein a length of the level sensor guide is 218 to 400 mm, and
   wherein a length of the concentration sensor guide is 40 to 80 mm.

2. The fuel sensor of claim 1, further comprising:
   a plate which is mounted on an upper surface of the pump module housing;
   a printed circuit board (PCB) case which is mounted on an upper surface of the plate and includes a PCB therein; and
   a cover which covers an upper surface of the PCB case.

3. The fuel sensor of claim 2, wherein an O-ring is provided between the plate and the PCB case.

* * * * *